United States Patent [19]
Michelet et al.

[11] 4,324,731
[45] Apr. 13, 1982

[54] PROCESS FOR THE PREPARATION OF 2,3-DIHYDRO-2,2-DIMETHYL-7-HYDROXYBENZOFURAN

[75] Inventors: Daniel Michelet, Tassin La Demi Lune; Serge Veracini, Lyons, both of France

[73] Assignee: Rhone-Poulenc Agrochimie, Lyons, France

[21] Appl. No.: 204,992

[22] Filed: Nov. 7, 1980

[30] Foreign Application Priority Data

Dec. 7, 1979 [FR] France .............................. 79 30645

[51] Int. Cl.$^3$ .......................................... C07D 307/86
[52] U.S. Cl. ............................................... 260/346.22
[58] Field of Search ..................................... 260/346.22

[56] References Cited

U.S. PATENT DOCUMENTS 3,470,299  9/1969  Heiss et al. ........................ 424/285
3,474,170 10/1969  Scharpf ............................. 424/285
3,474,171 10/1969  Scharpf ............................. 424/285
3,927,118 12/1975  Ozretich .......................... 260/613 D

FOREIGN PATENT DOCUMENTS 1179250  1/1970  United Kingdom .

OTHER PUBLICATIONS

Toth et al., Chem. Abstracts, 5106c, p. 479, vol. 91, (1979).
Newer Methods of Preparative Organic Chemistry, vol. II, pp. 337–359, (translation in English of German "Neuere Methoden der Präp. Org. Chem.", II, pp. 231–246) by Stroh et al.

Primary Examiner—Henry R. Jiles
Assistant Examiner—Bernard Dentz
Attorney, Agent, or Firm—Browdy and Neimark

[57]     ABSTRACT

Process for the preparation of 2,3-dihydro-2,2-dimethyl-7-hydroxybenzofuran from ortho-methallyloxyphenol or ortho-methallylpyrocatechol.

It consists in heating ortho-methallyloxyphenol or ortho-methallylpyrocatechol in the presence of an aluminum derivative.

2,3-Dihydro-2,2-dimethyl-7-hydroxybenzofuran can be used for the synthesis of carbofuran, which is a polyvalent insecticide.

14 Claims, No Drawings

PROCESS FOR THE PREPARATION OF 2,3-DIHYDRO-2,2-DIMETHYL-7-HYDROXYBENZOFURAN

The invention relates to a process for the preparation of 2,3-dihydro-2,2-dimethyl-7-hydroxybenzofuran.

This compound has the formula:

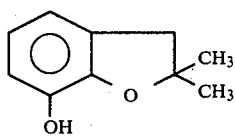

2,3-Dihydro-2,2-dimethyl-7-hydroxybenzofuran, hereafter designated by DDHB, is a compound which is in itself known and which can be used for the preparation of 2,3-dihydro-2,2-dimethylbenzofuran-7-yl methylcarbamate, this being a wide-spectrum/insecticide known by the name carbofuran.

It is known from U.S. Pat. No. 3,474,171 and British Pat. No. 999,128 that DDHB can be obtained by heating ortho-methallyloxyphenol, which results in a rearrangement of this compound by transposition of the methallyl radical, with the formation of pyrocatechol derivatives, and then cyclising some of the derivatives formed in this way (in particular the ortho-methallylpyrocatechol or 3-methallyl-1,2-dihydroxybenzene) to give DDHB.

According to these patents, this conversion is carried out by heating the ortho-methallyloxyphenol in bulk, at an elevated temperature, without the use of a catalyst, the yields of DDHB generally being low (48.2% of theory, according to British Pat. No. 999,128).

Ortho-methallyloxyphenol is the compound of the formula:

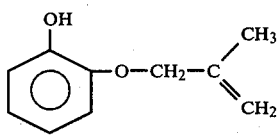

Ortho-methallylpyrocatechol is the compound of the formula:

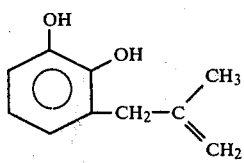

It is also known from Stroh et al., Neuere Methoden per Präparativen Org. Chem. [Recent Methods in Preparative Organic Chemistry], II, pages 231–246, and in particular page 245, that the heating of tert.-butyl phenyl ether in the presence of aluminium phenolates causes scission of this ether, with the liberation of isobutene, and attachment of this isobutene to the phenol to give ortho-tert.-butylphenol.

The process described by Stroh corresponds to the alkylation of phenols by an olefine, which is specifically orientated towards alkylation on the nucleus in the ortho position, relative to the hydroxyl. It further implies that an olefine can be formed by scission of the starting alkyl phenyl ether.

Ortho-methallyloxyphenol exhibits the characteristic of possessing both a phenol group and an unsaturation of the olefinic type. The application of operating conditions such as described by Stroh to the heating of ortho-methallyloxyphenol should therefore normally have led to an alkylation reaction in the ortho position, relative to the hydroxyl group, which can be written as follows:

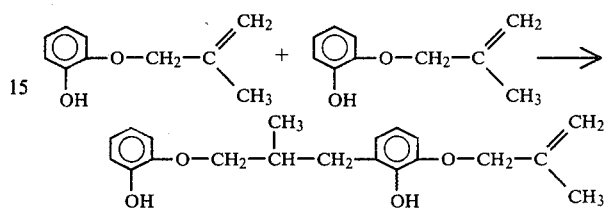

It is obvious that the reaction proposed by the invention is of an entirely different nature from that described by Stroh, because, according to the invention, there is attachment of a hydrocarbon chain in the meta position and not in the ortho position.

Finally, it is known from French Pat. No. 1,548,441 to prepare 2,3-dihydro-2,2-dimethyl-7-alkoxybenzofurans from 1-alkoxy-2-methallyloxybenzenes by rearranging these compounds to give 2-alkoxy-6-methallylphenols and then cyclising the latter compounds.

The process described by the said patent is different from that claimed by our application, because the final product, as well as the starting material and the product formed as an intermediate, are different "alkoxy" derivatives from those used in accordance with our application. Furthermore, the said patent in no way either describes or suggests the use, as catalysts, of the aluminium derivatives proposed by the present patent application.

One object of the present invention is to provide an improved process for the preparation of DDHB, in particular from ortho-methallylpyrocatechol.

A further object of the invention is to prepare DDHB from ortho-methallyloxyphenol with an improved yield.

A further object of the invention is to make it possible to prepare DDHB from ortho-methallyloxyphenol in essentially a single step, without having to isolate the compound or compounds formed as intermediates.

It has now been found that these objects can be achieved by virtue of the new process which forms the subject of the present invention.

This process is a process for the preparation of DDHB by heating ortho-methallylpyrocatechol; it comprises heating ortho-methallylpyrocatechol in the presence of an aluminium derivative as a catalyst.

Under these conditions, it is observed, unexpectedly, that DDHB is obtained with a high yield, at relatively low temperatures (e.g. 100° to 150° C.), whereas, in the absence of an aluminium derivative, the heating of ortho-methallylpyrocatechol at these same temperatures leads only to insignificant yields of DDHB or even to the formation of no DDHB at all.

Ortho-methallylpyrocatechol can be prepared by the thermal isomerisation of ortho-methallyloxyphenol, of the Claisen rearrangement type, by means of heating at a generally very elevated temperature (of the order of about 200° C.), advantageously in the presence of an inert organic solvent.

According to a preferred embodiment of the process of the invention, the rearrangement of orthomethallyloxyphenol to give ortho-methallylpyrocatechol is carried out by heating the ortho-methallyloxyphenol in the presence of an aluminium derivative. It is then observed that the presence of this aluminium derivative during the heating of ortho-methallyloxyphenol unexpectedly assists the rearrangement of this compound. It is therefore particularly advantageous to heat the ortho-methallyloxyphenol in the presence of an aluminium derivative and to continue this heating, in the presence of the same aluminium derivative, until DDHB is formed. Under these conditions, it is observed that the two successive conversions take place in an immediate sequence and that the ortho-methallylpyrocatechol is converted to DDHB as it is formed.

This gives a process which makes it possible to produce DDHB in a single step, from ortho-methallyloxyphenol, by heating the latter in the presence of an aluminium derivative.

This process, which forms part of the invention, thus relates to the preparation of DDHB by heating orthomethallyloxyphenol; it comprises heating ortho-methallyloxyphenol in the presence of an aluminium derivative. It constitutes the preferred embodiment of the invention.

According to a second embodiment of the process of the invention, ortho-methallyloxyphenol is first heated in the absence of an aluminium derivative, at an elevated temperature, in which case a partial or total conversion of the starting material takes place to give pyrocatechol derivatives (in particular ortho-methallylpyrocatechol), and the heating of the reaction medium containing these products formed as intermediates is subsequently continued in the presence of an aluminium derivative, which is then added to the reaction medium.

This also gives a process which makes it possible to prepare DDHB in a single step, from orthomethallyloxyphenol, without having to isolate the products formed as intermediates. This process, which also forms part of the invention, relates to the preparation of DDHB by heating ortho-methallyloxyphenol; it comprises initially heating ortho-methallyloxyphenol at a very elevated temperature, in the absence of an aluminium derivative, until the major part of the orthomethallyloxyphenol has been converted, and then subsequently continuing the heating in the presence of an aluminium derivative.

As aluminium derivatives which can be used according to the process of the invention, there may be mentioned the compounds of the formula:

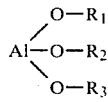

in which $R_1$, $R_2$ and $R_3$, which are identical or different, each represent an organic radical. Advantageously, $R_1$, $R_2$ and $R_3$ are chosen from amongst alkyl, cycloalkyl, aralkyl, aryl and benzofuryl radicals, these radicals themselves being optionally substituted.

More particularly, the aluminium derivatives used are those in which $R_1$, $R_2$ and $R_3$, which are identical or different, are chosen from amongst the following radicals: optionally halogen-substituted alkyl radicals containing from 1 to 20 carbon atoms, cycloalkyl radicals containing from 3 to 12 carbon atoms (e.g. cyclohexylmethyl), aralkyl radicals containing from 7 to 10 carbon atoms (e.g. benzyl), aryl radicals containing from 6 to 12 carbon atoms (e.g. phenyl, naphthyl and diphenyl), which are optionally substituted by 1 to 3 identical or different substituents chosen from amongst halogen atoms, hydroxyl radicals, alkyl or alkoxy radicals containing from 1 to 4 carbon atoms, (linear or branched) alkenyl or alkenyloxy radicals containing from 2 to 6 carbon atoms, and phenyl radicals, the benzofuryl radical which is optionally substituted by 1 to 4 identical or different radicals chosen from amongst alkyl radicals containing from 1 to 4 carbon atoms and alkenyl radicals containing from 2 to 4 carbon atoms (e.g. one or more of the radicals $R_1$, $R_2$ and $R_3$ can represent the 2,3-dihydro-2,2-dimethylbenzofuran-7-yl radical).

Aluminium derivatives which are preferably used are aluminium alcoholates, in particular aluminium lower alkylates, i.e. aluminium alcoholates in which each of the alkyl parts contains at most six carbon atoms, such as e.g. aluminium isopropylate, or aluminium phenolates, such as e.g. the aluminium-substituted derivative of ordinary phenol, aluminium cresolate and aluminium ortho-methallyloxyphenolate, which are optionally prepared in situ. For the purpose of the present application, the expression aluminium phenolate denotes in general terms the aluminium-substituted derivatives of the various phenols and must not therefore be restricted only to the derivative of ordinary phenol. Amongst these aluminium derivatives, aluminium isopropylate is preferably used.

The aluminium alcoholates and phenolates which can be used in the process of the invention can be prepared in accordance with methods which are in themselves known, e.g. by reacting aluminium with the appropriate alcohol or phenol in an anhydrous medium. Thus, the phenolate of the formula $(C_6H_5O)_3Al$ can be prepared in situ by reacting aluminium powder with phenol. The aluminium phenolates can also be prepared by reacting an aluminium alkylate or aluminium phenolate with the appropriate phenol.

The amount of aluminium derivatives to be used must be sufficient to enable the conversion to proceed satisfactorily. For this purpose, at least 0.0005 mol of aluminium derivative is generally used per mol of starting product to be converted, i.e. respectively per mol of ortho-methallylpyrocatechol in the case where this compound is used as the starting material, or per mol of ortho-methallyloxyphenol in the case where this compound is used as the starting material, according to the modified embodiments of the process of the invention. The upper limit of the amount of catalyst to be used is not critical. However, from 0.001 to 0.3 mol of aluminium derivative is preferably used per mol of starting material to be converted.

The temperature at which the ortho-methallylpyrocatechol or the ortho-methallyloxyphenol is heated, in the presence of the aluminium derivative, is advantageously between 80° and 250° C.; it is preferably between 100° and 200° C.

The conversion of the ortho-methallyloxyphenol or the ortho-methallylpyrocatechol to give DDHB, in accordance with the process of the invention, proceeds satisfactorily in the absence of any solvent.

It can also be carried out advantageously in the presence of an organic solvent, which is preferably chosen from amongst aromatic hydrocarbons, such as toluene or o-, m- and p-xylenes, aliphatic hydrocarbons, such as octane or decane, chlorinated aliphatic or aromatic hydrocarbons, such as 1,2-dichloroethane or 1,1,2-trichloroethane, cycloaliphatic hydrocarbons, such as cyclohexane, aliphatic or aromatic ethers, such as anisole, ketones, such as methyl isobutyl ketone, alcohols, such as lower alkanols, such as e.g. isopropanol, and phenols, more particularly phenol itself.

The conversion according to the invention is advantageously carried out under ordinary atmospheric pressure. However, it can be carried out under a pressure which is different from ordinary atmospheric pressure. Thus, if it is desired to use a solvent of which the b.p., under normal atmospheric pressure, is below the temperature at which it is desired to carry out the reaction, the conversion according to the invention can be carried out in an autoclave under a pressure which is greater than atmospheric pressure.

The time required to carry out the conversion according to the invention depends on the temperature used, i.e. this time is the shorter, the higher is the temperature. This time is generally between 15 minutes and twenty hours.

At the end of the reaction, the DDHB obtained is separated off by any means which is in itself known, such as e.g. by distillation. However, for certain uses, it may not be necessary to isolate the DDHB and it then suffices to leave it in the reaction medium, which is itself used in the desired manner. The aluminium derivative can be removed by washing the reaction mixture with an aqueous solution of a strong acid.

Ortho-methallyloxyphenol is a compound which is in itself known, the preparation of which has been described in French Patent Application No. 2,255,279.

The following examples, which are given without implying a limitation, illustrate the invention and show how it can be carried out.

For greater convenience, in the following examples, the notation "DC(ME)" will mean "degree of conversion of the ortho-methallyloxyphenol" and the notation "Y(DDHB)" will mean "yield of DDHB, relative to the ortho-methallyloxyphenol converted".

EXAMPLE 1:

The equipment used consists of a 20 ml round-bottomed flask fitted with a reflux condenser and a magnetic stirring bar.

Aluminium isopropylate (0.0207 g; $1.0.10^{-4}$ mol) and o-methallyloxyphenol (1.7012 g; $1.037.10^{-2}$ mols) are introduced successively into the flask.

The mixture is heated at 130° C. for 12 hours, whilst stirring, and then cooled to ambient temperature. A 2 N aqueous hydrochloric acid (20 ml) and ethyl acetate (20 ml) are then added and the whole is shaken vigorously in a separating funnel. After the two phases have been separated, the organic phase is washed with distilled water (20 ml) and the latter is then combined with the aqueous phase; this aqueous phase is in turn washed with ethyl acetate (20 ml) and the latter is combined with the first organic phase. The combined organic phases provide DDHB (1.208 g) and also contain unconverted ortho-methallyloxyphenol (0.195 g), i.e.:

DC(ME)=88.5%
Y(DDHB)=80.2%

COMPARISON EXPERIMENT:

By carrying out the reaction under the temperature and treatment conditions described in Example 1, starting from ortho-methallyloxyphenol (1.043 g), without using an aluminium derivative, a mixture containing unconverted ortho-methallyloxyphenol (0.189 g), DDHB (0.0126 g), ortho-methallylpyrocatechol (0.520 g) and para-methallylpyrocatechol (0.188 g) is obtained, i.e.:

DC(ME)=81.9%
Y(DDHB)=1.5%

(From this experiment, it will be observed that, at 130° C., in the absence of a catalyst, only a very small proportion of the ortho-methallylpyrocatechol cyclises to give DDHB, and that the DC(ME) is lower than that obtained with a catalyst.)

EXAMPLE 2:

The reaction is carried out in accordance with the same method as in Example 1, using the same equipment and starting from aluminium isopropylate (0.0436 g; $2.1.10^{-4}$ mols) and o-methallyloxyphenol (1.7164 g; $1.046.10^{-2}$ mols).

The mixture is heated at 140° C. for 6 hours, whilst stirring.

DDHB (1.080 g) is thus obtained and unconverted ortho-methallyloxyphenol (0.343 g) remains, i.e.:

DC(ME)=80.0%
Y(DDHB)=78.6%

EXAMPLE 3:

The reaction is carried out in accordance with the same method as in Example 1, using the same equipment and starting from aluminium isopropylate (0.0257 g; $1.2.10^{-4}$ mols) and o-methallyloxyphenol (2.2789 g; $1.4.10^{-2}$ mols).

The mixture is heated at 150° C. for 1 hour, whilst stirring:

DC(ME)=75.1%
Y(DDHB)=75.4%

EXAMPLE 4:

The reaction is carried out in accordance with the same method as in Example 1, using the same equipment and starting from aluminium isopropylate (0.239 g; $11.5.10^{-4}$ mols) and ortho-methallyloxyphenol (1.7548 g; $1.07.10^{-2}$ mols).

The mixture is heated at 150° C. for 15 minutes, whilst stirring:

DC(ME)=96.4%
Y(DDHB)=71.7%

EXAMPLE 5:

Aluminium isopropylate (0.266 g; $13.0.10^{-4}$ mols), o-methallyloxyphenol (2.156 g; $1.31.10^{-2}$ mols) and p-xylene (5 ml) are introduced successively into the equipment described in Example 1.

The mixture is heated at 140° C. for 2 hours 30 minutes, whilst stirring, and then cooled to ambient temperature. A 2 N aqueous hydrochloric acid (50 ml) and methylene chloride (50 ml) are then added and the whole is shaken in a separating funnel. After filtration through a Büchner funnel in order to remove the insoluble materials, and after separation of the two liquid phases, the aqueous phase is washed with methylene chloride (2×25 ml) and the latter is then combined with the organic phase.

The combined organic phases provide DDHB (1.666 g) and contain unconverted ortho-methallyloxyphenol (0.072 g), i.e.:

DC(ME)=96.6%

Y(DDHB)=79.9%

EXAMPLE 6:

The reaction is carried out in accordance with the same method as in Example 5, using the same equipment and starting from aluminium isopropylate (0.244 g; $12.10^{-4}$ mols), o-methallyloxyphenol (2.1658 g; $1.32.10^{-2}$ mols) and p-xylene (5 ml).

The mixture is heated at 120° C. for 3 hours 30 minutes, whilst stirring. DDHB (1.456 g) is thus obtained and unconverted ortho-methallyloxyphenol (0.298 g) remains, i.e.:
DC(ME)=86.2%
Y(DDHB)=78.0%

EXAMPLE 7:

The reaction is carried out in accordance with the same method as in Example 5, using the same equipment and starting from aluminium isopropylate (0.0252 g; $1.2.10^{-4}$ mols), ortho-methallyloxyphenol (2.4384 g; $1.5.10^{-2}$ mols) and xylene (6 ml).

The mixture is heated at 140° C. for 16 hours 30 minutes, whilst stirring:
DC(ME)=98.5%
Y(DDHB)=74.0%

EXAMPLE 8:

The reaction is carried out in accordance with the same method as in Example 5, using the same equipment and starting from aluminium isopropylate (0.132 g; $6.4.10^{-4}$ mols), ortho-methallyloxyphenol (2.002 g; $1.2.10^{-2}$ mols) and anisole (5 ml).

The mixture is heated at 130° C. for 6 hours, whilst stirring:
DC(ME)=86.9%
Y(DDHB)=74.8%

EXAMPLE 9:

The reaction is carried out in accordance with the same method as in Example 5, using the same equipment and starting from aluminium isopropylate (0.822 g; $40.10^{-4}$ mols), ortho-methallyloxyphenol (2.119 g; $1.3.10^{-2}$ mols) and n-decane (5 ml).

The mixture is heated at 100° C. for 1 hour, whilst stirring. This yields a mixture containing DDHB (1.286 g) and ortho-methallylpyrocatechol (0.177 g; $0.11.10^{-2}$ mol), but no longer containing ortho-methallyloxyphenol:
DC(ME)=100.0%
Y(DDHB)=60.7%

EXAMPLE 10:

Aluminium isopropylate (0.237 g; $11.6.10^{-4}$ mols), o-methallyloxyphenol (2.0473 g; $1.24.10^{-2}$ mols) and isopropyl alcohol (6 ml) are introduced successively into a 25 cc stainless steel autoclave.

The autoclave is heated at 150° C. for 3 hours in a bath consisting of a Wood's alloy, and then cooled to ambient temperature. The reaction mixture is then partially concentrated and subsequently taken up between a 2 N aqueous solution of hydrochloric acid (50 ml) and methylene chloride (50 ml). The remainder of the treatment is identical to that described in Example No. 5.

DDHB (1.564 g) is thus obtained and unconverted ortho-methallyloxyphenol (0.036 g) remains, i.e.:
DC(ME)=98.2%
Y(DDHB)=77.8%

EXAMPLE 11:

The reaction is carried out in accordance with the same method as in Example 10, in an autoclave into which aluminium isopropylate (0.263 g; $12.9.10^{-4}$ mols), ortho-methallyloxyphenol (2.0087 g; $1.22.10^{-2}$ mols) and n-decane (6 ml) are introduced.

The mixture is heated at 150° C. for 3 hours and then treated as indicated in Example 10:
DC(ME)=98.6%
Y(DDHB)=73.5%

EXAMPLE 12:

The reaction is carried out in accordance with the same method as in Example 10, in an autoclave into which aluminium isopropylate (0.263 g; $12.9.10^{-4}$ mols), ortho-methallyloxyphenol (2.284 g; $1.4.10^{-2}$ mols) and p-xylene (6 ml) are introduced.

The mixture is heated at 200° C. for 30 minutes and then treated as indicated in Example 10:
DC(ME)=99.6%
Y(DDHB)=71.0%

EXAMPLE 13:

Aluminium powder (0.039 g; $14:3.10^{-4}$ mols), depassivated beforehand by treatment with aqueous hydrochloric acid, o-methallyloxyphenol (2.186 g; $1.33.10^{-2}$ mols) and p-xylene (10 ml) are introduced successively into the equipment described in Example No. 1.

The mixture is heated at 140° C. Mercuric chloride (about 1 mg) is then added and there is an instantaneous evolution of gas. The reaction mixture is kept at 140° C. for 1 hour 30 minutes, whilst stirring, and it is then cooled to ambient temperature. The treatment is then identical to that described in Example No. 5.

DDHB (1.093 g) is thus obtained and unconverted ortho-methallyloxyphenol (0.768 g) remains, i.e.:
DC(ME)=64.9%
Y(DDHB)=77.1%

EXAMPLE 14:

$(C_6H_5O)_3Al$ (0.0305 g; $1.0.10^{-4}$ mol), prepared in a separate operation by reacting aluminium isopropylate with phenol, and o-methallyloxyphenol (1.6017 g; $9.77.10^{-3}$ mols) are introduced into the equipment described in Example 1.

The mixture is heated at 130° C. for 15 hours. It is then treated as indicated in Example 1 and this yields unconverted o-methallyloxyphenol (0.338 g) and DDHB (0.975 g), i.e.:
DC(ME)=78.9%
Y(DDHB)=75.6%

EXAMPLE 15:

Ortho-methallyloxyphenol (12.0 g), which is 96.4% pure and also contains 1.17% of DDHB, and n-octane (108 g) are introduced into a titanium autoclave. The mixture is heated at 200° C. for 1 hour 30 minutes and cooled. The reaction mixture is then concentrated until the n-octane has been completely removed. Analysis of the resulting crude product (11.93 g) then shows that the ortho-methallyloxyphenol has disappeared from the reaction medium and that essentially methallylpyrocatechols (mainly ortho-methallylpyrocatechol) have formed.

Aluminium isopropylate (0.013 g; $0.6.10^{-4}$ mol) and the crude product obtained above (1.3871 g) are introduced successively into the equipment described in Example 1.

The mixture is heated at 130° C. for 5 hours 30 minutes, whilst stirring, and then cooled to ambient temperature, and the treatment is then continued as indicated in Example 1.

This yields an ethyl acetate solution containing DDHB (0.960 g). This solution contains no ortho-methallyloxyphenol and no unconverted ortho-methallylpyrocatechol, i.e.:

Y(DDHB)=70.1%

We claim:

1. A process for the preparation of 2,3-dihydro-2,2-dimethyl-7-hydroxybenzofuran by heating orthomethallylpyrocatechol, which comprises heating ortho-methallylpyrocatechol in the presence of an aluminium derivative of the formula

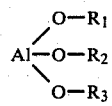

in which $R_1$, $R_2$ and $R_3$, which are identical or different, each represent an organic radical.

2. A process according to claim 1, wherein the ortho-methallylpyrocatechol is obtained by heating ortho-methallyloxyphenol.

3. A process according to claim 2, wherein the ortho-methallylpyrocatechol is obtained by heating ortho-methallyloxyphenol in the presence of an aluminium derivative.

4. A process according to claim 3, wherein the conversion of ortho-methallyloxyphenol to give 2,3-dihydro-2,2-dimethyl-7-hydroxybenzofuran is carried out in a single operation by heating in the presence of an aluminium derivative.

5. A process according to one of claims 1 to 4, wherein the heating in the presence of an aluminium derivative is carried out at a temperature between 80° and 250° C.

6. A process according to claim 5, which comprises using at least 0.0005 mol of aluminium derivative per mol of starting material to be converted.

7. A process according to claim 1, wherein the substituents $R_1$, $R_2$ and $R_3$ shown in the formula given in claim 7, which substituents are identical or different, each represent an optionally halogen-substituted alkyl radical containing from 1 to 20 carbon atoms, a cycloalkyl radical containing from 3 to 12 carbon atoms, an aralkyl radical containing from 7 to 10 carbon atoms, an aryl radical containing from 6 to 12 carbon atoms, which is optionally substituted by 1 to 3 identical or different substituents chosen from amongst halogen atoms, hydroxyl radicals, alkyl radicals containing from 1 to 4 carbon atoms, alkoxy radicals containing from 1 to 4 carbon atoms, alkenyl radicals containing from 2 to 6 carbon atoms, alkenyloxy radicals containing from 2 to 6 carbon atoms, and phenyl radicals, or the benzofuryl radical which is optionally substituted by 1 to 4 identical or different radicals chosen from amongst alkyl radicals containing from 1 to 4 carbon atoms and alkenyl radicals containing from 2 to 4 carbon atoms.

8. A process according to claim 7, wherein the aluminium derivative is an aluminium alcoholate or an aluminium phenolate.

9. A process according to claim 8, wherein the aluminium derivative is chosen from amongst aluminium lower alkylates, aluminium phenolate, aluminium cresolate and aluminium ortho-methallyloxyphenolate.

10. A process according to claim 9, which comprises using from 0.001 to 0.3 mol of aluminium derivative per mol of starting material to be converted.

11. A process according to claim 10 for the preparation of 2,3-dihydro-2,2-dimethyl-7-hydroxybenzofuran from ortho-methallyloxyphenol, which comprises heating ortho-methallyloxyphenol, in the presence of the aluminium derivative, at a temperature between 100° and 200° C.

12. A process according to claim 11, wherein the aluminium derivative is aluminium isopropylate.

13. A process according to one of claims 1 to 4, wherein the heating of the starting material, i.e. ortho-methallylpyrocatechol or ortho-methallyloxyphenol, is carried out in the presence of an organic solvent.

14. A process according to claim 5, wherein the heating of the starting material ortho-methallylpyrocatechol or ortho-methallyloxyphenol is carried out in the presence of an organic solvent.

* * * * *